United States Patent [19]

Chu et al.

[11] Patent Number: 5,420,261
[45] Date of Patent: May 30, 1995

[54] GLYCOSIDES OF 3'-DEOXYAQUAYAMYCIN ANTIBIOTICS

[75] Inventors: Min Chu, Union; Ann C. Horan, Summit, both of N.J.; Joseph A. Marquez, Evergreen, Colo.; Mahesh G. Patel, Verona, N.J.

[73] Assignee: Schering Corporation, Kenilworth, N.J.

[21] Appl. No.: 890,454

[22] Filed: May 29, 1992

[51] Int. Cl.⁶ .............................................. C07H 3/00
[52] U.S. Cl. ................... 536/18.1; 435/886; 536/6.4
[58] Field of Search ................ 536/6.4, 18.1; 514/25; 435/86

[56] References Cited

U.S. PATENT DOCUMENTS 4,973,673  11/1990  Sanada et al. ................. 536/6.4

OTHER PUBLICATIONS

T. Uchida, et al. The Journal of Antibiotics (1985) vol. 38 (No. 9) 1171–1181.

*Primary Examiner*—Douglas W. Robinson
*Assistant Examiner*—Elli Peselev
*Attorney, Agent, or Firm*—Thomas D. Hoffman

[57] ABSTRACT

Two novel glycosides of 3'-deoxyaquayamycin isolated from an antimicrobial complex produced in fermentation under controlled conditions using a biologically pure culture of the microorganism Streptomyces sp. SCC 2136, ATCC 55186 are disclosed.

3 Claims, No Drawings

GLYCOSIDES OF 3'-DEOXYAQUAYAMYCIN ANTIBIOTICS

This invention relates to two novel glycosides of 3'-deoxyaquayamycin. The compounds exhibit antibacterial and antifungal activity and are isolated from an antimicrobial complex which is produced in fermentation under controlled conditions using a biologically pure culture of the microorganism, Streptomyces sp. SCC 2136, ATCC 55186.

T. Uchida, et al. *The Journal of Antibiotics* Vol. 38 (#9) 1171–1181 (1985) disclose the antibiotics, saquayamycins A, B, C and D which are glycosides of aquayamycin. However, this reference does not disclose or make obvious the compounds of this invention.

SUMMARY OF THE INVENTION

The present invention embraces Streptomyces sp. SCC 2136, ATCC 55186 and mutants and variants thereof having the identifying characteristics of Streptomyces sp. SCC 2136.

Another aspect of the present invention is directed to the antimicrobial complex produced by cultivating a strain of Streptomyces sp. SCC 2136 having the identifying characteristics of ATCC 55186 in a temperature controlled medium having assimilable sources of carbon and nitrogen under controlled submerged aerobic conditions until a composition of matter having substantial antimicrobial activity is produced.

The present invention is also directed to two novel antibiotics isolated from the antimicrobial complex, i.e., a compound represented by the formula 1:

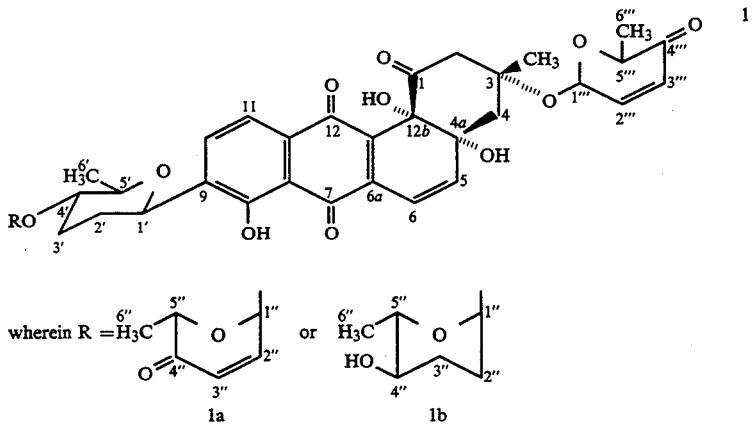

in substantially chemically pure form, or a pharmaceutically acceptable salt thereof.

THE MICROORGANISM

The microorganism used for the production of antimicrobial complex and the compounds represented by formula 1 is a biologically pure culture of Streptomyces sp. SCC 2135, ATCC 55186.

A viable culture of this microorganism has been deposited on May 22, 1991 in the collection of the American Type Culture Collection (ATCC) in Rockville, Md., where it has been assigned accession number ATCC 55186. Should the deposited culture become lost, destroyed or non-viable during the longer of the thirty (30) year period from the date the culture was deposited or the five (5) year period after the last request for the deposited culture or the effective life of the patent which issues from this application, the culture will be replaced upon notice by applicants or assignee(s) of this application. Subcultures of Streptomyces sp. SCC 2136, ATCC 55186 are available during the pendency of this application to one determined by the Commissioner of Patents and Trademarks to be entitled thereto under 37 CFR 1.14 and 35 USC 122 and will be available to the public without restriction once a patent based on this application is granted. Use of the microorganism is dependent on the U.S. Patent Laws.

The microorganism was isolated from a sample of soil collected in Edmonton, Alberta, Canada. It had been characterized and found to have the microscopic, macroscopic, and whole cell hydrolysis properties of the genus Streptomyces.

DESCRIPTION OF THE PRODUCING STRAIN: STREPTOMYCES sp.SCC 2136, ATCC 55186

Source material for the following taxonomic evaluations was a frozen preparation of a pure culture of Streptomyces sp. SCC 2136, ATCC 55186. Source materials used for these studies were frozen ($-80°$ C.) preparations of pure cultures. Inoculum for the biochemical and physiological tests were prepared by adding 1.0 ml of thawed culture suspension to 10 ml of broth in a test tube (or 2.5 ml to 50 ml of broth in a 250 ml flask) which was placed on a rotary shaker (250–300 RPM, 28°– 30° C.) for 3 to 5 days. The culture was harvested by centrifugation and, where appropriate, washed three times with distilled water by centrifugation. The final cell pellet was resuspended in distilled water to approximately 4 times the packed cell volume. Approximately 0.1 ml of this cell suspension was used to inoculate all the biochemical tests except for the plate hydrolysis studies where the inoculum was 0.2–0.3 ml. The incubation temperature for the biochemical and physiological tests was 30° C. Readings of the results were made at weekly intervals for 2 to 4 weeks for the plate media. Most of the tubed media were read at various times up to 28 days. The tests for decomposition of urea, allantoin and hippurate, as well as the tests for the reduction of nitrates were read for six weeks.

MORPHOLOGY

Morphological observations of the producing strain of the microorganism of this invention were made on plates of water agar, and inorganic salts-starch agar AV. Plates were incubated at 28° C. and observed for 2 to 3 weeks.

SCC 2136 is a gram-positive, filamentous organism that forms a well developed, moderately branching substrate mycelium with hyphae which are approximately 0.4–0.7 μm in diameter. Strain SCC 2136 produces an aerial mycelium with moderately branching hyphae. These hyphae bear straight to flexuous spore chains which are usually very long; spore chains of 30 to 60 or more spores are common. The spores are cylindrical, smooth-walled, and approximately 0.7–0.8 μm wide×0.8–2.0 μm long. No motile elements were observed in either the substrate or aerial mycelium.

CHEMOTAXONOMY

Whole-cell hydroysates of SCC 2136 were analyzed by the method of Lechevalier [Lechevalier, M. P., *J. Lab. Clin. Med.*, Vol. 71, pp. 934–944 (1968)] and shown to contain the L-form of diaminopimelic acid.

PHYSIOLOGICAL AND BIOCHEMICAL CHARACTERISTICS

The procedures used to obtain the captioned characteristics were those cited by Gordon [Gordon, R. E., *J. Gen. Microbiol.*, Vol. 45, pp. 355–364 (1966)], Luedemann and Brodsky [Luedemann and Brodsky, "*Antimicrob. Agents Chemother.*" pp 47–52 (1965)] and Horan and Brodsky [Horan and Brodsky, *Int. J. Syst. Bacteriol.*, Vol. 32, pp. 195–200 (1982)]. The producing strain of the microorganism of this invention, SCC 2136, produces acid from adonitol, D-amygdalin, D-arabinose, L-arabinose, D-cellobiose, dextrin D-fructose, L-fucose, D-galactose, glucose, glycerol, i-inositol, inulin, lactose maltose, D-mannitol, D-mannose, α-D-melibiose, α-methyl-D-glucoside, α-methyl-D-glucopyranoside, D-raffinose α-L-rhamnose, D-ribose, salicin, sucrose, D-trehalose and D-xylose but not from dulcitol, i-erythritol, L-sorbose or D-sorbitol. Adenine, hypoxanthine, L-tyrosine, potato starch, urea, xylan and casein are hydrolyzed but, hippurate and hydantoin are not. Gelatin is liquified. Nitrate is not reduced to nitrite. Melanin is formed. Growth does not occur at 45° C. Growth is poor at 37° C. The microorganism of this invention, SCC 2136, grows poorly at 10% NaCl; good growth occurs at 6, 7, 8, and 9% NaCl but not at 12.5%. Acetate, butyrate, citrate, formate, fumurate, glutamate, gluconate, α-keto-glutarate, lactate, malate, malonate, oxalate, propionate, pyruvate and succinate are utilized; but benzoate, oleate and tartrate are not.

Physiological and Biochemical Characteristics

The physiological characteristics of SCC 2136 are presented in Table I. Acid production from carbohydrates and carbohydrate utilization are shown in Table II.

DESCRIPTION OF STREPTOMYCES sp. SCC 2136 ON VARIOUS MEDIA

Macroscopic Description

The growth characteristics of SCC 2136 on various media are presented in Table III. All plates were incubated at 28° C. and observed at intervals up to 3 weeks. The common names for the colors were chosen after comparison with color chips from the ISCC-NBS Centroid Color Charts (Office of Standard Reference Materials, NBS Circular 553, National Bureau of Standards, Washington, D.C.) or The Color Harmony Manual, 4th Ed., 1958. (Container Corporation of America, Chicago).

The vegetative mycelium of SCC 2136 varies from grayish yellowish brown to reddish brown to brownish black. At three weeks, the aerial mycelium varies from white to yellowish pink to pink except on water agar, whereon the aerial mycelium is occasionally pale gray. Strain SCC 2136 produces brown to brownish black to black melanin pigments in the agar on many media. However, on Czapek sucrose agar and starch agar the soluble pigment is reddish brown.

CONCLUSION

On the basis of the above morphological and chemotaxonomic characteristics, SCC 2136 was determined to be a species of Streptomyces.

TABLE I

Physiological Characteristics of *Streptomyces sp.* SCC 2136, ATCC 55186

| Test | Results |
| --- | --- |
| Formation of Melanin | + |
| Liquifacation of Gelatin | + |
| Hydrolysis of Decomposition of: | |
| Adenine | + |
| Allantoin | V |
| Casein | + |
| Hippurate | − |
| Hydantoin | − |
| Hypoxanthine | + |
| L-Tyrosine | + |
| Potato Starch | + |
| Urea | + |
| Xanthine | V (42 days) |
| Xylan | + (42 days) |
| Reduction of Nitrate | − |
| Utilization of: | |
| Acetate | + |
| Benzoate | − |
| Butyrate | + |
| Caprylate | V |
| Citrate | + |
| Formate | + |
| Fumurate | + |
| Glutamate | + |
| Gluconate | + |
| Glucuronate | VW |
| Lactate | + |
| Malate | + |
| Malonate | + |
| Oleate | − |
| Oxalate | + |
| Propionate | + |
| Pyruvate | + |
| Succinate | + |
| Tartrate | − |
| α-Keto-glutarate | + |
| Calcium glycerate | V |
| Growth at: | |
| 5° C. | + |
| 10° C. | + |
| 28° C. | + |
| 37° C. | + (Poor) |
| 40° C. | VW |
| 42° C. | VW |
| 45° C. | − |
| Growth of NaCl: | |
| 6.0% | + |
| 7.0% | + |
| 8.0% | + |
| 9.0% | + |
| 0.0% | VW |
| 2.5% | − |

+ = positive; − = negative; V = variable; VW = variable and only weakly positive; +(42 days) positive after 42 days.

TABLE II

Acid Production from Carbohydrates and
Carbohydrate Utilization for *Streptomyces sp.*
SCC 2136, ATCC 55186

| Carbohydrate | Acid Production | Carbohydrate Utilization |
|---|---|---|
| Adonitol | + | + |
| D-Amygdalin | + | VW |
| D-Arabinose | + | VW |
| L-Arabinose | + | + |
| D-Cellobiose | + | + |
| Dextrin | + | + |
| Dulcitol | − | − |
| i-Erythritol | − | − |
| D-Fructose | + | + |
| L-Fucose | + | + |
| D-Galactose | + | + |
| Glucose | + | + |
| Glycerol | + | + |
| i-Inositol | + | + |
| Inulin | + | + |
| Lactose | + | + |
| Maltose | + | + |
| D-Mannitol | + | + |
| D-Mannose | + | + |
| D-Melezitose | ± | − |
| D-Melibiose | + | + |
| α-Methyl-D-glucoside | + | + |
| α-Methyl-D-mannoside | + | + |
| D-Raffinose | + | + |
| L-Rhamnose | + | + |
| D-Ribose | + | + |
| Salicin | + | + |
| D-Sorbitol | − | VW |
| L-Sorbose | − | − |
| Sucrose | + | + |
| D-Trehalose | + | + |
| D-Xylose | + | + |

+ = positive; − = negative; ± = doubtful VW = variable and only weakly positive

TABLE III

Description of Streptomyces sp. SCC 2136 ATCC 55186 on Various Media

| | | |
|---|---|---|
| Bennett Agar | G | Fair, grayish yellowish brown (ISCC-NBS 80) to dark grayish yellowish brown (ISCC-NBS 81) |
| | AM | Sparse, white |
| | SC | None to sparse |
| | SP | Moderate yellowish brown (ISCC-NBS 77) to deep yellowish brown (ISCC-NBS 75) |
| Glycerol-Asparagine Agar (ISP 5) | G | Good, coco brown (CHM 5ni) to deep brown (CHM 5pl) |
| | AM | Sparse to moderate, white |
| | SC | Moderate |
| | SP | Deep brown (CHM 4pl) to dark luggage tan (CHM 4pg) |
| Glucose-Yeast Extract Agar | G | Excellent, dark brown (ISCC-NBS 59) to dark grayish brown (ISCC-NBS 62) |
| | AM | Sparse, white |
| | SC | Sparse |
| | SP | Dark brown (ISCC-NBS 59) to black (ISCC-NBS 267) |
| Water Agar | G | Poor, translucent |
| | AM | Sparse, white to pale gray (CHM gray scale b), cottony |
| | SC | Moderate to numerous |
| | SP | None |
| Yeast Extract-Malt Extract Agar (ISP 2) | G | Excellent, deep red brown (CHM 6½ PI) |
| | AM | Moderate, white |
| | SC | Moderate to numerous |
| | SP | Light brown (CHM 4ng) to chestnut brown (CHM 4ni) |
| Oatmeal Agar (ISP 3) | G | Fair to good, brick red (CHM 6ng) to deep brown mahogany (CHM 6pl) |
| | AM | Sparse to moderate, white to pinkish white (ISCC-NBS 9) |
| | SC | Sparse to moderate |
| | SP | Russet brown (CHM 4pi) to deep brown (CHM 4pl) |
| Inorganic Salts - Starch Agar (ISP 4) | G | Good, old wine (CHM 7ng) to burgundy (CHM 7pl) |
| | AM | Moderate, white to pinkish white (ISCC-NBS 9), cottony |
| | SC | Numerous |
| | SP | Grayish yellow (ISCC-NBS 90) to dark grayish yellow (ISCC-NBS 91) |
| Starch Agar (Waksman #21) | G | Fair, dark brown (CHM 5pn) to deep brown mahogany (CHM 6pl) |
| | AM | Moderate, white turning pale pink (CHM 6ca) to rose pink (CHM 7½ ea) |
| | SC | Sparse to moderate |
| | SP | Moderate reddish brown (ISCC-NBS 43) |

TABLE III-continued

Description of Streptomyces sp. SCC 2136 ATCC 55186 on Various Media

| | | |
|---|---|---|
| Peptone-Yeast Extract-Iron Agar (ISP 6) | G | Fair, grayish yellowish brown (ISCC-NBS 80) to dark grayish yellowish brown (ISCC-NBS 81) |
| | AM | None |
| | SC | None |
| | SP | Brownish black (ISCC-NBS 65) to black (ISCC-NBS 267) |

FERMENTATION OF THE MICROORGANISM

The antimicrobial complex of this invention is produced when the microorganism, Streptomyces sp. SCC 2136, ATCC 55186 is grown in an aqueous nutrient medium under submerged aerobic conditions at a temperature of about 27° C. to 40° C., preferably at from 27° C. to 35° C., and at a pH of from about 6.5 to 8.0 with agitation until substantial antimicrobial activity is imparted to the medium. The pH of the medium is monitored but not controlled. Temperature studies indicate that the organism grows rapidly at about 30° C. Therefore, the fermentation is preferably conducted at a temperature of 30° C. for a period of about 24 to about 96 hours preferably about 90 hours.

To determine when peak antimicrobial production has been reached, samples of the fermentation broth were assayed every 24 hours (starting at 48 hours.) for antimicrobial activity by bioassay of the whole broth against Staohvlococcus aureus ATCC 209P (pH 8.0), Escherichia coli ATCC 10536 (pH 8.0) and Candida albicans Wisconsin. The growth of the organism (packed cell volume), pH and dissolved oxygen levels are determined either intermittently or continuously.

As nutrient medium, there is employed any suitable medium containing a source of carbon, for example an assimilable carbohydrate, and a source of nitrogen, for example an assimilable nitrogenous or proteinaceous material and various mineral salts.

The medium employed for the fermentation contained beef extract, tryptone, yeast extract, cerelose and soluble starch as the major sources of nitrogen and carbon, respectively. Under these conditions, the microorganism, SCC 2136, produced the antimicrobial complex containing at least two major components 1a and 1b which are biologically active components of the complex as determined by bioautography against both S. aureus, E. coli and C. abicans after development of a thin layer chromatography plate in 2:2:1 (v/v/v) chlorofrom: methanol: pH 3.5 acetate buffer.

The foregoing media are exemplary of the nutrients utilized by Streptomyces sp. to produce the antimicrobial complex of this invention. However, it is obvious to those trained in the fermentation science that a wide range of nutrients obtained from a number of suppliers may be substituted for the foregoing, and that generally good growth and antibiotic production can be obtained, such nutrients being the functional equivalent to those set forth herein.

The fermentation is conducted by initially sterilizing the fermentation medium prior to the addition of the inoculum.

The pH of the fermentation medium is generally monitored and found to be in the range of from 6.5 to 8.0; a pH range of from 6.5 to 7.5 is typical. Prior to sterilization, the pH of the medium is usually adjusted to 7.5 and prior to inoculation, the pH is usually adjusted to 7.0.

The fermentation was initiated by addition of the inoculum to the broth. Generally, inoculum volume is 5.0% of total broth volume. The inoculum is prepared by addition of a sample of the frozen whole broth to an appropriate medium. A particularly preferred medium comprises beef extract, 0.3%; tryptone, 0.5%; cerelose, 0.1% soluble starch, 2.4%; yeast extract, 0.5%; and calcium carbonate, 0.2% (all percents by weight). The pH of the inoculum medium is adjusted to 7.5 prior to sterilization. There were two inoculum stages of the fermentation, each of which usually required from 24 to 120 hours with 2 to 4 days preferred and is generally conducted in the preferred medium listed hereinabove at about 30° C. with agitation. Agitation and a positive air flow, generally about 3.5 L/min. and a temperature of about 30° C. are employed during tank fermentations which lasted 90 hours. The fermentation medium consisted; of PD-650 dextrin, 30 g/L; pea flour, 15.0 g/L; maltose, 5.0 g/L; fructose, 5.0 g/L; molasses (dark), 5 mL/L and sea salts, 0.1 g/L.

ISOLATION AND PURIFICATION OF THE COMPOUNDS OF THIS INVENTION

The antimicrobial complex of this invention contains a mixture of two compounds as represented by formula I. The procedure for the isolation of 1a and 1b is summarized in Scheme 1. The fermentation broth was first filtered through filter paper. The filtration was then absorbed onto XAD-16 resin and eluted with a MeOH-$H_2O$ gradient. The active fraction of XAD-16 eluant was purified by silica gel column chromatography eluting with cholorform. The active complex was further loaded onto LH-20 Sephadex column. The column was eluted with cholorform-methanol solvent mixture (1:1 v/v) to obtain an active mixture of 1a and 1b. Compounds 1a and 1b were finally separated and purified by silica gel column chromatography with gradient containing 0 to 5% MeOH in $CHCl_3$ (v/v). Both compounds 1a and 1b appear as red-orange powders, and are soluble in dichlormethane, chloroform and dimethyl sulfoxide, less soluble in methanol, diethyl ether and ethyl acetate, and insoluble in hexane and water. The compounds 1a and 1b give a negative response to ninhydrin and Rydon tests.

Scheme 1

Whole Broth (10 L)
↓ Filtration

Filtrate
↓ XAD-16 Column
  [MeOH—H₂O gradient]

Acitve Fraction
↓ Silica gel column
  [CHCl₃]

Active Complex
↓ LH-20 Column
  [CHCl₃—MeOH 1:1]

Acitive Mixture
↓ Silica Gel Column
  [0–5% MeOH in CHCl₃]

Chromatography

↓ ↓

1a (40 mg)   1b (15 mg)

CHEMICAL DEGRADATION AND STRUCTURE ELUCIDATION

The UV spectra of 1a and 1b in MeOH were similar to that of saquayamycins. The molecular weights of 1a and 1b were determined by the negative-ion FAB-MS technique. The $^1$H NMR and $^{13}$C NMR spectra indicated the presence of an aglycone as well as two hexose moieties. The physicochemical data for compounds 1a, 1b and the hydrolysis products and 2a and 3a are summarized in Table IV. All the data revealed molecular formula of 1a and 1b to be $C_{37}H_{38}O_{13}$, and $C_{37}H_{42}O_{13}$, respectively. The $^1$H and $^{13}$C NMR data of 1a and 1b along with their hydrolysis products 2a and 3a are listed in Tables V and VI, respectively. To further confirm these assignments and determine the regiochemistry, degradations of 1a and 1b have been carried out and summarized in Scheme II hereinbelow

Scheme II 3a 3'-Deoxyaquayamycin

Hydrolysis of 1a with 0.05N HCl—MeOH at room temperature for 1 hour produced a pigment 2a. After a purification on silica gel column with 1% MeOH in CHCl₃, 2a was recovered reaction. The further hydrolysis of 2a at 85° C. with 0.1N HCl—MeOH for 1 hour yielded 3a.

$^1$H and $^{13}$CNMR spectral data of 2a indicated the lack of one L-aculose unit in comparison with 1a . Particularly, $^{13}$C NMR data suggested that a L-aculose attached to carbon-3 was hydrolyzed because the carbon-3 signal shifted up-field. Both the $^1$H and the 13C, NMR spectra of 3a revealed that another L-aculose was hydrolyzed from 2a. The analysis of spectroscopic data concluded that aglycone 3a was 3'-deoxyaguayanycin due to the absence of hydroxyl functional group an carbon-3' by comparison with aquayamycin.

The difference between compound 1b and 1a was a sugar unit connected to carbon-4'. The saturated sugar in 1b was identified as an L-amicetose based on the NMR data analysis. As shown in Scheme II, the hydrolysis product of 1b was found to be identical to aglycone 3a, the hydrolysis product of 2a. This evidence supported the assignment of structure to 1b. Furthermore, the determination of stereochemistry for aglycone and sugar units was accomplished by decoupling experiments as well as the correlation to aquayanycin.

TABLE IV

PHYSICO-CHEMICAL PROPERTIES OF 1a, 1b, 2a AND 3a

| | 1a | 1b | 2a | 3a |
|---|---|---|---|---|
| Appearance | Reddish-Orange Powder | Red Powder | Red Powder | Red Powder |
| FAB-MS (−eV) | 690 (M)⁻ | 694 (M)⁻ | 580 (M)⁻ | 469 (M-H)⁻ |
| Molecular Formula | $C_{37}H_{38}O_{13}$ | $C_{37}H_{42}O_{13}$ | $C_{31}H_{32}O_{11}$ | $C_{25}H_{26}O_9$ |
| M.P. °C. (dec.) | 168 ~ 169 | 151 ~ 153 | 162 ~ 163 | 165 ~ 167 |
| IR (KBr.)vmax cm⁻¹ | 3440(br.) 2936, 1728, 1700, 1640, 1276, 1261, 1087, 1041 | 3450(br.) 2934, 1728, 1699, 1641, 1276, 1261, 1086, 1052, 1263, 1090, 1052, | 3430(br.) 2931, 1721, 1639, 1621, 1434, 1295, 1279, 1262, 1090, 1053 | 3425(br.) 2930, 1723, 1639, 1621, 1435, 1295, 1279, |
| UV (MeOH)λmax nm | 218,320,436 | 218,321,438 | 219,317,436 | 219,318,440 |

TABLE V

¹H NMR of Compound 1a, 1b, 2a and 3a[i]

| Proton | 1a | 1b | 2a | 3a |
|---|---|---|---|---|
| 2-CH₂ ax | 2.55 d[ii] (13 Hz)[iii] | 2.53 d (13.2 Hz) | 2.63 d (13.0 Hz) | 2.62 d (13 Hz) |
| eq | 3.23 dd (3, 13 Hz) | 3.21 dd (13, 13.2 Hz) | 2.96 dd (3, 13 Hz) | 2.96 dd (3, 13 Hz) |
| 4-CH₂ ax | 1.83 d (15.7 Hz) | 1.81 d (15.4 Hz) | 7.83 d (15.0 Hz) | 1.83 d (15, 13 Hz) |
| eq | 2.48 dd (3, 15.7 Hz) | 2.46 dd (13, 15.4 Hz) | 2.28 dd (3, 15 Hz) | 2.26 dd (13, 15 Hz) |
| 5-H | 6,42 d (9.8 Hz) | 6.40 d (9.8 Hz) | 6.41 d (9.8 Hz) | 6.41 d (9.8 Hz) |
| 6-H | 6.92 d (9.8 Hz) | 6.90 d (9.8 Hz) | 6,91 d (9.8 Hz) | 6.91 d (9.8 Hz) |
| 8-OH | 12.31 s | 12.28 s | 12.30 s | 12.29 s |
| 10-H | 7.89 d (7.9 Hz) | 7.87 d (7.8 Hz) | 7.90 d (7.8 Hz) | 7.89 d (7.8 Hz) |
| 11-H | 7.63 d (7.9 Hz) | 7.60 d (7.8 Hz) | 7.63 d (7.8 Hz) | 7.61 d (7.8 Hz) |
| 13-CH₃ | 1.48 s | 1.47 s | 1.30 s | 1.30 s |
| 1'-H | 4.83 br.d (9.8 Hz) | 4.80 br.d (9.8 Hz) | 4.83 br.d (9.8 Hz) | 4.80 br.d (9.8 Hz) |
| 2'-CH₂ ax | 1.82 m | 1.80–2.20 m | 1.82 m | 1.40 m |
| eq | 2.25 m | | 2.23 m | 2.20 m |
| 3'-CH₂ | 2.28 m | ~2.25 m | 2.29 m | 1.66 m |
| 4'-H | 3.42 m | 3.46 m | 3.41 m | 3.42 m |
| 5'-H | 3.58 dq (6.1, 9.1 Hz) | 3.54 dq (6, 9 Hz) | 3.58 dq (6, 9 Hz) | 3.55 dq (6, 9 Hz) |
| 6'-CH₃ | 1.35 d (6.1 Hz) | 1.31 d (6.2 Hz) | 1.37 d (6.7 Hz) | 1.38 d (6.2 Hz) |
| 1"-H | 5.33 d (3.5 Hz) | 4.70 brs. | 5.33 d (3.5 Hz) | |
| 2"-H | 6.85 dd (3.5, 10.1 Hz) | 1.80 m | 6.84 dd (3.5, 10.2 Hz) | |
| 3"-H | 6.12 d (10.2 Hz) | ~2.20 m | 6.11 d (10.2 Hz) | |
| 4"-H | | 3.43 m | | |
| 5"-H | 4.61 q (6.7 Hz) | 3.73 dq (6, 9 Hz) | 4.61 q (6.8 Hz) | |
| 6"-CH₃ | 1.38 d (6.7 Hz) | 1.23 d (6.2 Hz) | 1.39 d (6.7 Hz) | |
| 1'''-H | 5.59 d 3.5 (Hz) | 5.58 d (3.5 Hz) | | |
| 2'''-H | 6.70 dd (3.5, 10.1 Hz) | 6.69 dd (3.5, 10.1 Hz) | | |
| 3'''-H | 6.08 d (10.2 Hz) | 6.06 d (10.2 Hz) | | |
| 5'''-H | 4.75 q (6.7 Hz) | 4.73 q (6.7 Hz) | | |
| 6'''-CH₃ | 1.44 d (6.7 Hz) | 1.43 d (6.7 Hz) | | |

[i]= Recorded at 300 MHz in CDCl₃, chemical shifts in PPM from TMS.
[ii]= Multiplicity
[iii]= Coupling Counstant

TABLE VI

³C NMR of Compounds 1a, 1b, 2a and 3a[i]

| Carbon | 1a | 1b | 2a | 3a |
|---|---|---|---|---|
| Aglycone | | | | |
| 1 | 204.1 | 204.2 | 204.6 | 205.1 |
| 2 | 50.2 | 50.2 | 51.9 | 52.1 |
| 3 | 82.7 | 82.8 | 75.8 | 76.1 |
| 4 | 42.6 | 42.6 | 43.0 | 43.2 |
| 4a | 79.2 | 79.3 | 80.3 | 80.6 |
| 5 | 145.2 | 145.2 | 144.0 | 144.3 |
| 6 | 117.5 | 117.4 | 117.4 | 117.5 |
| 6a | 138.8 | 138.7 | 138.6 | 138.7 |
| 7 | 188.0 | 188.1 | 187.8 | 187.9 |
| 7a | 113.8 | 113.8 | 113.7 | 113.8 |
| 8 | 158.0 | 158.3 | 158.1 | 158.3 |
| 9 | 138.4 | 138.4 | 137.9 | 138.1 |
| 10 | 133.6 | 133.7 | 133.5 | 133.7 |
| 11 | 119.8 | 119.8 | 119.7 | 119.8 |
| 11a | 130.2 | 130.1 | 130.0 | 130.0 |
| 12 | 182.3 | 182.3 | 181.9 | 182.1 |
| 12a | 139.3 | 139.8 | 199.3 | 139.6 |
| 12b | 77.1 | 77.4 | 77.1 | 76.0 |
| 13 | 26.5 | 26.5 | 30.1 | 30.2 |
| 1' | 70.7 | 69.8 | 70.3 | 71.9 |
| 2' | 31.5 | 31.6 | 31.4 | 31.9 |
| 3' | 31.8 | 31.9 | 31.6 | 33.0 |
| 4' | 80.8 | 79.1 | 80.6 | 78.8 |
| 5' | 76.7 | 77.4 | 76.0 | 73.0 |
| 6' | 18.5 | 18.5 | 18.3 | 18.3 |
| Sugar 1 | | | | |
| 1" | 94.9 | 98.1 | 94.8 | |
| 2" | 142.8 | 27.6 | 142.7 | |
| 3" | 127.7 | 30.0 | 127.2 | |
| 4" | 196.8 | 72.0 | 196.0 | |
| 5" | 73.1 | 73.0 | 72.9 | |
| 6" | 15.2 | 17.8 | 15.0 | |
| Sugar 2 | | | | |
| 1''' | 88.7 | 88.7 | | |
| 2''' | 142.9 | 142.9 | | |
| 3''' | 127.4 | 127.6 | | |
| 4''' | 196.8 | 196.9 | | |
| 5''' | 70.4 | 70.6 | | |
| 6''' | 15.1 | 15.1 | | |

[i]Recorded at 75 MHz in CDCl₃, Chemical Shifts in ppm from TMS.

THE BIOLOGICAL ACTIVITY OF THE ANTIMICROBIAL COMPLEX, THE COMPOUNDS OF FORMULAS 1a AND 1b

The antimicrobial complex of this invention exhibits antifungal activity in vitro and activity against Gram positive and Gram negative microorganisms.

The compounds represented by formula 1, isolated from the antimicrobial complex exhibits in vitro antifungal in a Sabouraud dextrose broth medium against eight species of Candida (geometric mean MIC of $\geqq 43$ mcg/mL) and seven species of dermatophytes (geometric mean MIC of $\geqq 5$ mcg/mL). The biological activates of compounds 1a, 1b and adriamycin are reported in Table VI hereinbelow

TABLE VI
BIOLOGICAL ACTIVITY GEOMETRIC MEAN MIC (µg/ml)

| Medium/Microorganism | COMPOUND | | |
|---|---|---|---|
| | 1a | 1b | Adriamycin |
| SAB[1] - Candida (8 species) | $\geqq 43$ | $\geqq 128$ | $\geqq 128$ |
| SAB[2] - Dermatophytes (seven species) | $\geqq 5$ | $\geqq 132$ | $\geqq 128$ |
| EMEM[2] - Mycelial | 78 | 95 | 128 |

[1]SAB = Sabouraud Dextrose Broth Medium
[2]EMEM = Eagles Medium Essential Medium The compounds represented by formula 1 also exhibit in vitro antibacterial activity.

PHARMACEUTICAL COMPOSITIONS

This invention also contemplates antimicrobially effective pharmaceutical compositions comprising an antimicrobially effective amount of a compound of formula 1 or pharmaceutically acceptable salts thereof in admixture with a pharmaceutically acceptable, nontoxic carrier adapted for topical, oral or parenteral use.

The preferred pharmaceutically acceptable salts are nontoxic salts formed by adding to the compounds of the present invention about a stoichiometric amount of a suitable organic or inorganic base. Suitable organic bases include primary, secondary and tertiary alkyl amines, alkanolamines, aromatic amines, alkylaromatic amines and cyclic amines. Exemplary organic amines include the pharmaceutically acceptable bases selected from chloroprocaine, procaine, piperazine, glucamine, N-methylglucamine, N,N-dimethylglucamine, ethylenediamine, diethanolamine, diisopropylamine, diethylamine, N-benzyl-2-phenylethylamine, N-N'dibenzylethylenediamine, choline, clemizole, tris(hydroxymethyl)aminomethane, or D-glucosamine. The preferred organic bases include N-methyl glucamine ("NMG"), diethanolamine, and tris(hydroxymethyl)aminomethane ("TRIS"). The suitable inorganic bases include alkali metal hydroxides such as sodium hydroxide and divalent metal hydroxides such as the alkaline earth hydroxides, calcium hydroxide and barium hydroxide.

The topical, oral and parenteral dosage forms may be prepared according to procedures well known in the art, and may contain a variety of ingredients.

In the case of topical formulations, e.g., ointments, creams, lotions, powders, tablets, pessaries or sprays, the formulation will contain about 0.1 to 10 grams of a compound of formula 1 per 100 grams of carrier.

Oral dosage forms include tablets, capsules, elixirs, suspensions, and the like. Tablets contain such excipients as starch or lactose; liquid forms may contain coloring or flavoring agents.

Parenteral forms to be injected intravenously, intramuscularly, or subcutaneously are usually in the form of a sterile solution, and may contain salts or glucose to make the solution isotonic.

In general, the dosage of compound of formula 1 administered to combat a given microbial infection is similar to the dosage requirements of the present commercial products miconazole, clotrimazole, and ketoconazole.

In general, the topical dosage range of the compound of formula 1 is from about 0.1% to about 10% by weight of a particular pharmaceutical composition formulated in single or divided doses, with the preferred range being about 0.5% to about 4% and with the most preferred range being about 1% to about 2%.

In general, the oral dosage for humans of the compound of formula 1 administered to combat a given microbial infection ranges from about 1 mg per kilogram of body weight to about 50 mg per kilogram of body weight per day, in single or divided doses, with about 2 mg per kilogram of body weight to about 20 mg per kilogram of body weight per day being preferred.

In general, the parenteral dosage for humans of the compound of formula 1 administered to combat a given microbial infection ranges for about 0.1 mg per kilogram of body weight per day, to about 20 mg per kilogram of body weight per day, in single or divided doses, with about 1 mg per kilogram of body weight per day being preferred.

It will be appreciated that the actual preferred dosages of the compound of this invention or pharmaceutically acceptable salts thereof will vary according to the particular composition formulated, the mode of application and the particular situs, host and disease being treated. Many factors that modify the action of the drug will be taken into account by the attending clinician, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests.

The following examples illustrate the invention:

EXAMPLE 1

Preparation of the Antimicrobial Complex of This Invention

A. Inoculum Preparation
1) Initial Stage
Prepare a 250 mL Erlenmeyer flask with 70 mL of the following germination medium:

| Beef Extract | 3 g |
|---|---|
| Tryptone | 5 g |
| Yeast Extract | 5 g |
| Cerelose | 1 g |
| Soluble Starch | 24 g |
| Calcium Carbonate | 2 g |
| Tap Water | 1000 mL |
| AF-1* | 1 mL |

*AF-1 is an antifoam agent available from Dow Corning Corp., Midland, MI 48641.

Adjust the pH of the germination broth to 7.5. Sterilize the broth and after cooling, add 3.5 mL of a frozen whole broth sample of the microorganism of this invention from a previously prepared inoculum to each flask broth. Incubate at 30° C. with continual agitation at 300 rpm for 48 hours. The inoculum stage was repeated under the same conditions.

2) Second Stage

Transfer 25 mL of the second stage germination broth to each of twenty 2-liter Erlenmeyer flasks, each containing 500 mL of the same germination medium and which had been previously pH adjusted and sterilized.

Incubate at 30° C. with continual agitation at 300 rpm for 48 hours.

B. Fermentation

| PD-650 Dextrin | 30.0 g/L |
| Maltose | 5.0 g/L |
| Pea Flour | 15.0 g |
| Fructose | 5.0 g/L |
| Molasses (Dark) | 5 mL/L |
| Sea Salts | 0.1 g/L |
| Yeast Extract | 3.0 g/L |
| NZ-Amine A | 3.0 g/L |
| Tap H2O adjust to | 1000.0 ml |
| Antifoam (AF-1 Dow Corning) | 0.5 ml |

Adjust the pH of the medium to 7.5 and then sterilize the medium. Inoculate the fermentation medium with 500 mL of the second stage inoculum preparation of Step A. Incubate the fermentation mixture at 30° C. with an air flow of 0.35 vvm and 350 rpm agitation for about 90 hours.

C. Isolation

Filter 10 L of the fermentation broth through filter paper. Absorb the flitrate on Amberlite XAD-16 by stirring it with the XAD-16 resin for 20 minutes. Elute the so-prepared XAD-16 resin with gradient MeOH-H2O solvent system. Lyophilyze the active fractions (100% MeOH eluant) to obtain a brown powder, Chromotograph the brown powder on a silica gel column with CHCl3 to produce an active complex as reddish powder.

What is claimed is:

1. The compound represented by the formula 1:

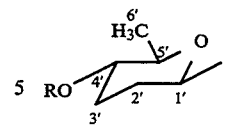

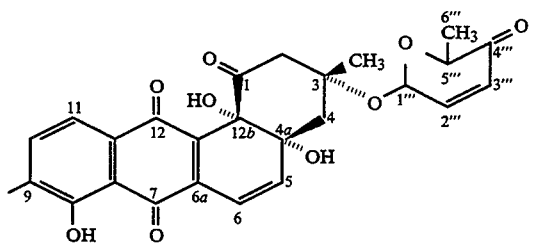

wherein R =

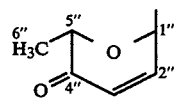

1a or

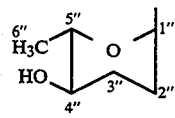

1b or a pharmaceutically acceptable salt thereof.

2. The compound of formula 1 wherein

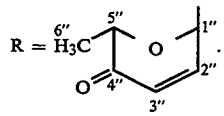

1a

3. The compound of formula 1 wherein

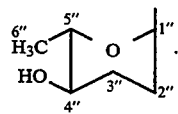

1b

* * * * *